United States Patent
Endo et al.

(10) Patent No.: US 7,335,801 B2
(45) Date of Patent: Feb. 26, 2008

(54) POLYGLYCEROLS AND PRODUCTION THEREOF

(75) Inventors: Toshio Endo, Ohtake (JP); Hidetoshi Omori, Ohtake (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 1 day.

(21) Appl. No.: 11/510,594

(22) Filed: Aug. 28, 2006

(65) Prior Publication Data

US 2007/0049775 A1   Mar. 1, 2007

(30) Foreign Application Priority Data

Sep. 1, 2005   (JP) ............................. 2005-253311

(51) Int. Cl.
*C07C 29/32* (2006.01)
*C07C 29/34* (2006.01)
*C07C 41/03* (2006.01)

(52) U.S. Cl. ...................... 568/867; 568/866; 568/680; 568/620; 568/679; 568/619; 568/699

(58) Field of Classification Search ................ 568/866, 568/867, 680, 620, 679, 619, 699
See application file for complete search history.

(56) References Cited

U.S. PATENT DOCUMENTS

| 4,973,763 A | 11/1990 | Jakobson et al. |
| 4,992,594 A | 2/1991 | Jakobson et al. |

FOREIGN PATENT DOCUMENTS

JP   61-140534 A   6/1986

*Primary Examiner*—Elvis O. Price
(74) *Attorney, Agent, or Firm*—Birch, Stewart, Kolasch & Birch, LLP

(57) ABSTRACT

A polyglycerol composition contains diglycerol, triglycerol, and tetraglycerol each in a content of 5 percent by weight or more, has a total content of diglycerol, triglycerol, and tetraglycerol of 75 percent by weight or more, has a total content of higher polyglycerol components of 10 percent by weight or less, the higher polyglycerol components each having a degree of polymerization of 7 or higher, and is substantially free from chlorine atom. A process prepares a polyglycerol composition by reacting glycerol and/or a polyglycerol with glycidol in the presence of an activated carbon catalyst.

7 Claims, No Drawings

POLYGLYCEROLS AND PRODUCTION THEREOF

BACKGROUND OF THE INVENTION

1. Field of the Invention

The present invention relates to polyglycerols. It also relates to processes of preparing polyglycerols in which glycerol and/or a polyglycerol such as diglycerol is reacted with glycidol in the presence of an activated carbon catalyst.

2. Description of the Related Art

Polyglycerols are widely used as moisturizing agents, thickening agents, and plasticizers. They are also used as raw materials for polyglycerol fatty acid esters that are used as emulsifiers for food additives, cosmetics, and medical materials.

Materials for food additives must comply with various specifications or standards, such as the specifications specified by the Joint FAO/WHO Expert Committee on Food Additives established by the Food and Agriculture Organization (FAO) and the World Health Organization (WHO). According to the specifications, for example, glycerol fatty acid esters for food additives must have a total content of diglycerol, triglycerol, and tetraglycerol of 75% or more, and a total content of polyglycerols each having carbon atoms equal to or more than heptaglycerol of 10% or less. In addition, they are preferably free from compounds harmful to the human body.

Polyglycerols have been conventionally prepared by heating and condensing glycerol in the presence of an alkali catalyst. This preparation process, however, invites by-production of branched-chain and cyclic glycerols, in addition to straight-chain glycerols, and the composition of the product cannot be significantly controlled. In addition, such cyclic glycerols are harmful to the human body and should be minimized.

Possible alternates for this preparation process are a process of allowing α-monochlorohydrin of glycerol or diglycerol with an alkali metal glycerolate and/or alkali metal diglycerolate (for example, U.S. Pat. No. 4,973,763) and a process of reacting glycerol-α-monochlorohydrin with epichlorohydrin in the presence of an acid or a compound with an acid reaction (for example, U.S. Pat. No. 4,992,594). These processes, however, use chlorine-containing compounds such as monochlorohydrin and epichlorohydrin as starting materials, and chlorine atoms cannot be fully removed from products polyglycerols. Thus, they are not desirable in view of safety, health, and environment.

To avoid these problems, proposed is a process of preparing polyglycerols using chlorine-free materials, in which glycerol or a polyglycerol is reacted with glycidol in the presence of a sulfonic acid ion-exchange resin catalyst (for example, Japanese Unexamined Patent Application Publication (JP-A) No. Sho 61-140534). The product polyglycerol mixture prepared according to this process, however, has a high degree of polymerization, and no polyglycerol product having a composition complying with the specifications has been obtained. In addition, the process requires repeated ion exchange procedures, thus inevitably has complicated steps, and invites high cost as an industrial preparation process.

As is described above, no polyglycerol composition has yet been developed which has a composition complying with the specifications, is free from chlorine and other harmful substances, and is suitable as a food additive.

SUMMARY OF THE INVENTION

Accordingly, an object of the present invention is to provide a polyglycerol composition having a specific composition and being substantially free from chlorine component. Another object of the present invention is to provide a process of preparing a polyglycerol composition using an activated carbon catalyst.

After intensive investigations, the present inventors have found that these objects can be achieved by carrying out ring-opening polymerization of glycidol with glycerol and/or diglycerol or a higher polyglycerol using an activated carbon as a catalyst. The present invention has been achieved based on these findings.

Specifically, the present invention provides a polyglycerol composition which contains diglycerol, triglycerol, and tetraglycerol each in a content of 5 percent by weight or more, has a total content of diglycerol, triglycerol, and tetraglycerol of 75 percent by weight or more, has a total content of higher polyglycerol components of 10 percent by weight or less, the higher polyglycerol components each having a degree of polymerization of 7 or higher, and is substantially free from chlorine atom.

The total content of cyclic polyglycerols in the polyglycerol composition is preferably 10 percent by weight or less.

The polyglycerol composition preferably has contents of tin atom, titanium atom, zinc atom, aluminum atom, copper atom, magnesium atom, phosphorus atom, and sulfur atom of each less than 1 ppm.

The present invention further provides a process of preparing a polyglycerol composition, including the step of reacting glycerol and/or a polyglycerol with glycidol in the presence of an activated carbon catalyst.

The process preferably further includes the steps of reacting glycerol with glycidol in the presence of the activated carbon catalyst; and removing unreacted glycerol from the resulting polyglycerol composition.

In the process, diglycerol can be reacted with glycidol in the presence of an activated carbon catalyst.

The polyglycerol composition according to the present invention is preferably prepared by the process mentioned above.

The process according to the present invention can prepare a polyglycerol composition containing substantially no chlorine component and no metal component and containing less cyclic components. The process can control the polyglycerol composition to have a specific composition. The resulting polyglycerol composition is particularly excellent from the viewpoints of safety and environment, complies with the specifications as food additives, and are useful as additives and raw materials typically for food and medical materials.

Further objects, features and advantages of the present invention will become apparent from the following description of the preferred embodiments.

DESCRIPTION OF THE PREFERRED EMBODIMENTS

The polyglycerol composition according to the present invention is a mixture of polyglycerols having different degrees of polymerization, such as glycerol, diglycerol, triglycerol, and tetraglycerol.

The polyglycerol composition according to the present invention comprises diglycerol, triglycerol, and tetraglycerol each in a content of 5 percent by weight or more. The content of each of these components is preferably 7 percent by weight or more, and more preferably 10 percent by weight or more. For example, a composition comprising diglycerol alone is not the polyglycerol composition according to the present invention. The diglycerol, triglycerol, and tetraglycerol herein refer to straight-chain polyglycerols. Hereinafter, all the polyglycerols refer to "straight-chain" polyglycerols, unless specified as "cyclic" or "branched-chain".

The polyglycerol composition according to the present invention has a total content of diglycerol, triglycerol, and tetraglycerol of 75 percent by weight or more based on the total weight of the polyglycerol composition, so as to comply with the specifications for food additives specified by JECFA (hereinafter briefly referred to as the "specifications").

The polyglycerol composition according to the present invention has a total content of higher polyglycerol components of 10 percent by weight or less, which higher polyglycerol components each have a degree of polymerization of 7 or higher, so as to comply with the specifications. The higher polyglycerol components each having a degree of polymerization of 7 or higher herein refer to, for example, heptaglycerol having a degree of polymerization of 7; octaglycerol having a degree of polymerization of 8; nonaglycerol having a degree of polymerization of 9; and higher polyglycerols.

The polyglycerol composition according to the present invention comprises substantially no chlorine atom, typically from the viewpoint of safety as food additives. The phrase "being substantially free from chlorine atom" means that the product polyglycerol composition has a chlorine atom content of 10 ppm or less, and more preferably 1 ppm or less.

The polyglycerol composition according to the present invention has a glycerol content of preferably 5 percent by weight or less, and more preferably 1 percent by weight or less, based on the total weight of the polyglycerol composition, typically from the viewpoint of safety as food additives.

The polyglycerol composition according to the present invention has a total content of cyclic polyglycerols of preferably 10 percent by weight or less, and more preferably 5 percent by weight or less, based on the total weight of the polyglycerol composition, typically from the viewpoint of safety as food additives.

The contents of metal components (metal elements), and elements derived from an acid catalyst in the polyglycerol composition according to the present invention are each preferably 1 ppm or less, and more preferably 0.5 ppm or less, based on the total weight of the polyglycerol composition. The elements herein include all the metal elements, as well as phosphorus and sulfur derived from, for example, phosphoric acid and sulfuric acid, respectively. The polyglycerol composition preferably satisfy the requirements upon tin atom, titanium atom, zinc atom, aluminum atom, copper atom, phosphorus atom, and sulfur atom. If any of the contents of these elements exceeds 1 ppm, the resulting polyglycerol composition may be unsuitable typically from the viewpoint of safety as food additives, or the produced polyglycerol composition may deteriorate or be colored with elapse of time.

The process of preparing a polyglycerol composition according to the present invention comprises the step of reacting glycerol and/or a polyglycerol with glycidol as starting materials, in the presence of an activated carbon catalyst.

The preparation process according to the present invention can further comprise the step of removing unreacted glycerol from a polyglycerol mixture prepared as a result of the reaction. The process particularly preferably comprises this removing step when glycerol is used as a starting material in the reaction.

The glycerol and/or polyglycerol for use as a raw material in the preparation process according to the present invention can comprise glycerol or a polyglycerol (e.g., diglycerol or triglycerol) alone; a mixture of glycerol and a polyglycerol such as diglycerol; or a mixture of polyglycerols. It preferably comprise glycerol or a polyglycerol having a single degree of polymerization, for controlling the degree of polymerization of the product. Among such glycerols, glycerol or diglycerol is preferably used for reducing polyglycerols having a high degree of polymerization, of which diglycerol is most preferably used, for low cost and simple production steps. It is acceptable to prepare polyglycerols having higher molecular weights by using, as a raw material, a polyglycerol having a higher degree of polymerization than diglycerol. In this case, the polyglycerol used as the raw material is preferably a polyglycerol prepared by the preparation process according to the present invention.

The glycerol and diglycerol for use as a raw material in the preparation process according to the present invention can be prepared by a conventional preparation process or are commercially available.

The glycidol for use as a raw material in the preparation process according to the present invention can be prepared by a conventional preparation process or is commercially available.

The activated carbon catalyst or use in the preparation process according to the present invention can be one conventionally known as a porous carbonaceous adsorbent. Such activated carbons can be prepared by carbonizing a carbonaceous material by heating, and activating the carbonized material. The materials herein include, but are not limited to, naturally occurring carbonaceous materials derived from animals, vegetables, and minerals, such as coal, cokes, pitch, bone charcoal (animal charcoal), vegetable charcoal, coconut shells/wood, sawdust, lignin, and beef bones; organic polymers including synthetic resins such as phenolic resins and polyacrylonitriles; and soot.

The activated carbon catalyst for use in the present invention can comprise an activated carbon alone or partially comprise an activated carbon. The catalyst can be, for example, an activated carbon supported on a carrier such as a plastic, a mineral, a ceramic, or a fiber; granules of an activated carbon prepared by granulating a powdery activated carbon with a binder; or granules granulated typically from a mineral or ceramic powder and a powdery activated carbon. Examples of the activated carbon catalyst partially comprising an activated carbon also include bone charcoal, vegetable charcoal, graphite, and carbon black, because these substances inherently comprise an activated carbon in their structure.

The specific surface area of the activated carbon catalyst for use in the present invention is not specifically limited, is generally about 500 $m^2/g$ or more, preferably about 750 $m^2/g$ or more, and more preferably about 900 $m^2/g$ or more. The upper limit thereof is generally about 3000 $m^2/g$.

The activated carbon catalyst for use in the present invention can have any shape, such as granular, powdery, fibrous, sheet-like, or honey-comb.

Such activated carbon catalysts for use in the present invention include, but are not limited to, granular activated carbons such as products of Calgon Mitsubishi Chemical Corporation (Japan) under the trade names of "F400, F300, PCB, BPL, CAL, CPG, and APC", products of Japan EnviroChemicals, Ltd. (Japan) under the trade names of "Granular Shirasagi WH and Granular Shirasagi C", products of Kuraray Chemical Co., Ltd. (Japan) under the trade name of "KURARAYCOAL KW", products of KUREHA CORPORATION (Japan) under the trade name of "BAC", and products of NORIT Japan Co., Ltd. (Japan) under the trade names of "PN, ZN, SA, SA-SW, SX, CA, CN, CG, D-10, W, GL, and HB PLUS"; powdery activated carbons such as products of Japan EnviroChemicals, Ltd. (Japan) under the trade names of "Shirasagi A and Shirasagi C"; fibrous activated carbons such as products of Toho Rayon Co., Ltd. (Japan) under the trade name of "FX-300", products of Osaka Gas Co., Ltd. (Japan) under the trade name of "M-30", and products of Toyobo Co., Ltd. (Japan) under the trade name of "KF-1500"; and sheet-like activated carbons such as products of KANEBO (Japan) under the trade name of "Microlite AC".

The amount of the activated carbon catalyst is not specifically limited, and is preferably about 0.01 to about 10 parts by weight, and more preferably about 0.1 to about 2 parts by weight, to 100 parts by weight of glycidol. The activated carbon catalyst used in an amount of exceeding 10 parts by weight may invite increased cost or cause decreased handleability such as stirring failure during the reaction. The activated carbon catalyst used in an amount of less than 0.01 parts by weight may not sufficiently exhibit its catalytic activity.

Activated carbons are more harmless and more safety in handling or in health, even if they remain in products, and are thereby more suitable typically for food additives than conventional metal catalysts and acidic catalysts. The activated carbon catalyst can be easily separated from the reaction mass (reaction mixture) by precipitation, filtration, and/or centrifugation, or carrying out the reaction using the catalyst as a packed column. In other words, the activated carbon catalyst for use in the present invention can be easily separated after the reaction and does not remain in the product. In contrast, conventional acidic catalysts, for example, cannot be easily separated from the reaction mass.

Additionally, the use of an activated carbon as the catalyst prevents coloring of the product, because such an activated carbon inherently has adsorptivity and acts to decolorize and deodorize. The decolorization and deodorization actions are particularly satisfactorily exhibited in reactions where an activated carbon is present in the reaction system from early stages of the reaction, as in the use as a catalyst in the present invention, although such actions are also obtained by purifying the product with an activated carbon such as in the case where the activated carbon is used as an adsorbent.

In addition, activated carbons are also economically preferred, because they are reusable repeatedly. The regeneration procedure for the activated carbon catalyst used in the present invention is not specifically limited and can be any conventional procedure such as vacuum regeneration in which the solute concentration in the solvent or the pressure is reduced to desorb adsorbed substances; solvent regeneration in which adsorbed substances are extracted with a solvent; substitution regeneration in which adsorbed substances are replaced by the action of another adsorptive substance; desorption by heating; chemical regeneration by chemical treatment; and oxidative decomposition regeneration as a result of oxidation and decomposition.

The preparation process according to the present invention may further use reaction diluents, antioxidants, ultraviolet absorbents, antifoaming agents, and viscosity adjusters, in addition to glycerol and/or a polyglycerol, glycidol, and the activated carbon catalyst.

Reaction diluents for use in the preparation process according to the present invention include, for example, solvents such as toluene, chloroform, acetone, methyl ethyl ketone, cyclohexanone, N,N-dimethylformamide, dioxane, and tetrahydrofuran.

The preparation process according to the present invention can be concretely carried out in the following manner. A mixture of glycerol and/or a polyglycerol with glycidol is placed in a reactor equipped with a heater and a stirrer, the mixture is heated to a predetermined temperature with stirring and mixing, and the temperature is maintained until the reaction completes. The raw materials can be mixed before they are placed in the reactor, but they can also be admixed by placing glycerol and/or a polyglycerol, and other components such as a solvent used according to necessity in the reactor, and thereafter adding glycidol dropwise thereto. The activated carbon catalyst can be placed in a reactor after mixing with the above mixture. Alternatively, the catalyst is placed in a packed column to form an activated carbon catalyst, through which the mixture passes, and a reaction is carried out. Where necessary, the reaction system may further comprise oxygen in such a concentration as to be effective for polymerization inhibition and to be safe.

The preparation process according to the present invention can be carried out in any system such as a batch system, semi-batch system, or continuous system. The reactor for use in the present invention can be any conventional reactor and is preferably an agitation tank, a circulation reactor such as a packed column, or a fluidized-bed reactor.

The activated carbon catalyst for use in the present invention is separated typically by centrifugation or filtration after the completion of the reaction. A packed column reactor is preferably employed, because there is no need of separation of the catalyst typically by filtration. The activated carbon catalyst which has lost its activity as a result of the reaction can be reused in the reaction after reactivating the same, for example, by steam regeneration and drying.

The reaction temperature and time in the preparation process according to the present invention vary depending on the types of the raw materials and activated carbon catalyst and are not specifically limited. The reaction temperature, however, is preferably about 120° C. to about 200° C., and the reaction time is preferably about 5 to about 60 hours. A reaction carried out at temperatures exceeding about 200° C. may invite side reactions and decomposition to thereby induce cyclic components and branched-chain components and/or coloring of the product. A reaction carried out at temperatures lower than about 120° C. requires a longer reaction time and may invite increased cost and/or decreased yield. A reaction conducted for a period exceeding 60 hours may invite increased cost and/or decreased production capability. In contrast, a reaction conducted for a period less than 5 hours may be difficult to control.

When the step of removing unreacted glycerol is included in the preparation process according to the present invention, the step can be carried out according to a conventional procedure and is preferably carried out, for example, by a vacuum removal procedure. The step of removing is effective when glycerol is contained in the raw material polyglycerol such as diglycerol, as impurities, and it is particularly effective when glycerol itself is used as the raw material.

A polyglycerol composition obtained by the preparation process according to the present invention is a mixture mainly comprising polyglycerols such as diglycerol, triglycerol, tetraglycerol, and other higher polyglycerols having a higher degree of polymerization.

The preparation process according to the present invention can easily control the reaction and can realize a total content of diglycerol, triglycerol, and tetraglycerol of 75 percent by weight or more. The process can also suppress branched-chain polyglycerols and cyclic polyglycerols, because the reaction can be carried out at relatively low temperatures as compared with a reaction in a heating and condensing process. In addition, the process can easily control the total content of higher polyglycerol components each having a degree of polymerization of 7 or higher to 10 percent by weight or less, because the product prepared by the process has a narrow distribution of degree of polymerization.

The product prepared by the process according to the present invention theoretically contain no chlorine atom, because the process does not use chlorine-containing raw materials and catalysts, such as epichlorohydrin. Additionally, the product contains substantially no metal element, because the process does not use metal catalysts.

Polyglycerol fatty acid esters can be obtained by subjecting the polyglycerol composition according to the present invention to esterification with fatty acids. The esterification can be carried out according to a conventional procedure, such as a procedure of carrying out esterification in the presence of, or in the absence of, a catalyst such as a base catalyst or an acid catalyst under ordinary pressure (atmospheric pressure) or under reduced pressure.

To convert the polyglycerol composition according to the present invention into fatty acid esters, the charged proportions of the polyglycerol composition and the fatty acid can be appropriately set according to the target use and required properties, such as hydrophilicity or hydrophobicity, of the product. To obtain a hydrophilic surfactant, for example, the weight proportions of these components are calculated from the hydroxyl value or number-average molecular weight of the polyglycerol components and the molecular weight of the fatty acid so that the number of moles of the polyglycerol components is equal to or higher than that of the fatty acid. To obtain a lipophilic surfactant, the number of moles of the fatty acid may be set higher than that of the polyglycerol components.

The resulting polyglycerol fatty acid esters may further be purified according to requirements as products. The purification can be carried out according to a conventional procedure. For example, it can be carried out by adsorption with activated carbon or activated clay; treatment under reduced pressure typically using steam or nitrogen gas as a carrier gas; washing with an acid and/or a base; or molecular distillation. In addition or alternatively, unreacted polyglycerol and other unnecessary components may be separated and removed typically by liquid-liquid distribution or by using an adsorbent, a resin, a molecular sieve, a loose reverse osmosis membrane, or an ultrafiltration membrane.

The polyglycerol fatty acid esters may further comprise additives such as antioxidants, ultraviolet absorbents, antifoaming agents, and viscosity adjusters. For example, for adjusting the viscosity, one or more of ethanol, propylene glycol, glycerol, water, liquid sugar, and oils and fats may be added and dissolved or emulsified therein. The polyglycerol fatty acid esters may further comprise the polyglycerol composition according to the present invention. They may be formed into powders by adding polysaccharides such as lactose and dextrin, or proteins such as caseinate.

The resulting polyglycerol fatty acid esters may be combined with one or more other surfactants to form surfactant preparations or compositions. Examples of the other surfactants are nonionic, amphoteric, anionic, and cationic surfactants including lecithins such as soybean lecithin, yolk lecithin, and rapeseed lecithin, and partially hydrolyzed products thereof; monoglycerides such as caprylic acid monoglyceride, capric acid monoglyceride, lauric acid monoglyceride, myristic acid monoglyceride, palmitic acid monoglyceride, stearic acid monoglyceride, behenic acid monoglyceride, oleic acid monoglyceride, elaidic acid monoglyceride, ricinoleic acid monoglyceride, and monoglyceride of condensed ricinoleic acid, mixtures of these monoglycerides, and organic acid monoglycerides as esters of these monoglycerides with organic acids such as acetic acid, citric acid, succinic acid, malic acid, and tartaric acid; sorbitan fatty acid esters such as sorbitan caprylate, sorbitan caprate, sorbitan laurate, sorbitan myristate, sorbitan palmitate, sorbitan stearate, sorbitan behenate, sorbitan oleate, sorbitan elaidate, sorbitan ricinoleate, and sorbitan ester of condensed ricinoleic acid; propylene glycol fatty acid esters such as propylene glycol caprylate, propylene glycol caprate, propylene glycol laurate, propylene glycol myristate, propylene glycol palmitate, propylene glycol stearate, propylene glycol behenate, propylene glycol oleate, propylene glycol elaidate, propylene glycol ricinoleate, and propylene glycol ester of condensed ricinoleic acid; sucrose fatty acid esters such as sucrose caprylate, sucrose caprate, sucrose laurate, sucrose myristate, sucrose palmitate, sucrose stearate, sucrose behenate, sucrose oleate, sucrose elaidate, sucrose ricinoleate, and sucrose ester of condensed ricinoleic acid.

[Determinations of Properties]

Examples of determination methods of properties of polyglycerol compositions herein will be illustrated below.

(1) Chlorine Content

The chlorine content was determined by potentiometric titration using an automatic titrator (HIRANUMA SANGYO CORPORATION, "COM-1600ST") in accordance with the method specified in Japanese Industrial Standards (JIS) K 7243-3:2005. The minimum limit of detection herein is 0.1 ppm.

(2) Elementary Analysis (Contained Elements and Contents Thereof)

The following elements including metals and phosphorus were identified and their contents were quantitatively analyzed using an inductively coupled plasma (ICP) atomic emission spectrometer (Shimadzu Corporation, "ICPS8100"). Samples were calcined with concentrated sulfuric acid, melted with potassium hydrogen sulfate, dissolved in diluted nitric acid, and subjected to determination. The minimum limit of detection is 0.1 ppm.

Analyzed elements: Al, As, Ba, Ca, Cd, Ce, Co, Cu, Cr, Ga, Ge, Fe, Hf, La, Li, Mg, Mn, Mo, Na, Ni, P, Pb, Sb, Se, Si, Sn, Sr, Ti, V, Zn, and Zr Sulfur was analyzed by an oxidative decomposition-ultraviolet fluorescence method in accordance with the method specified in JIS K 2541-6:2003.

(3) Color (APHA)

The color (hue) was determined in accordance with JIS K 1557:1970. A sample having an APRA (Hazen Color Number [Platinum Cobalt Standard]) of less than 100 was evaluated as showing no coloring (Good), and a sample having an APHA of 100 or more was evaluated as being colored (Poor).

(4) Acid Value, Hydroxyl Value, and Water Content

These were determined in accordance with JIS K 1557:1970.

(5) Viscosity

The viscosity was determined at 26° C. using an E-type viscometer.

(6) Compositional Analysis of Polyglycerols

The compositions of sample polyglycerols were analyzed by gas chromatography under following conditions. Samples were subjected to pretreatment before determination, in which each 0.03 g of the samples was mixed with 0.5 ml of pyridine, 0.5 ml of N-O-bistrimethylsilylacetamide, and a few drops of chlorotrimethylsilane, and the mixture was held at 50° C. for 30 minutes.

Device: Hewlett-Packard, "HP-6890"

Column: HP-5 having an inner diameter of 0.53 mm, a membrane thickness of 1.5 μm, and a length of 30 m Column temperature: held to 60° C. for one minute, elevated at a rate of 10° C./min, and held to 300° C. for 35 minutes.

Inlet temperature: 330° C.

Injection: Split injection with a split ratio of 40:1

Sample amount: 1 μL

EXAMPLES

The present invention will be illustrated in further detail with reference to several Examples and Comparative Examples below, which by no means limit the scope of the present invention.

Example 1

In a 1-liter four-necked flask equipped with a nitrogen inlet tube, a stirrer, a condenser, a temperature adjuster, and a dropping cylinder were placed 10.0 mol (920.9 g) of glycerol and 8.16 g (1.1 parts by weight to 100 parts by weight of glycidol) of an activated carbon catalyst (a product of Japan EnviroChemicals, Ltd. under the trade name of "Shirasagi A"; powdery activated carbon), and the mixture was heated to 120° C. Next, 10.0 mol (740.8 g) of glycidol was added dropwise over six-hours while keeping the reaction temperature to 120° C., and the reaction was continued until the oxirane concentration in the reaction system became less than 0.1 percent by weight based on the total weight of the reaction mixture. The oxirane concentration was sequentially determined by extracting part of the reaction mixture. Next, the temperature was elevated to about 200° C., the system was gradually evacuated using a vacuum pump to increase the degree of vacuum, and the residual glycerol was thus removed to a content of 1 percent by weight or less. After cooling, the activated carbon was removed from the reaction system by filtration, and thereby about 1650 g of a reaction product was obtained.

The prepared polyglycerol composition has a composition within the range as specified in the present invention and shows excellent properties without coloring, as shown in Table 1. The chlorine content and metal component contents of the polyglycerol composition are each below the minimum limit of detection (0.1 ppm).

Example 2

In a 2-liter four-necked flask equipped with a nitrogen inlet tube, a stirrer, a condenser, a temperature adjuster, and a dropping cylinder were placed 10.0 mol (1666.2 g) of diglycerol (Sakamoto Yakuhin Kogyo Co., Ltd.) and 12.016 g (1.3 parts by weight to 100 parts by weight of glycidol) of an activated carbon (a product of Japan EnviroChemicals, Ltd. under the trade name of "Shirasagi A"; powdery activated carbon), and the mixture was heated to 120° C. Next, 10.0 mol (740.8 g) of glycidol was added dropwise over six hours while keeping the reaction temperature to 120° C., and the reaction was continued until the oxirane concentration in the reaction system became less than 0.1 percent by weight based on the total weight of the reaction mixture. After cooling, the activated carbon was removed from the reaction system by filtration, and thereby about 2500 g of a reaction product was obtained.

The prepared polyglycerol composition has a composition within the range as specified in the present invention and shows excellent properties without coloring, as shown in Table 1. The chlorine content and metal component contents of the polyglycerol composition are each below the minimum limit of detection (0.1 ppm).

Comparative Example 1

In a 2-liter two-layer reactor (heating liquid: oil, inert gas atmosphere: nitrogen) were placed 12 mol (1326 g) of glycerol-α-monochlorohydrin and 2 ml of SnCl$_4$, and the mixture was heated to about 60° C. Next, 12 mol (1110 g) of epichlorohydrin was added dropwise over two hours while keeping the reaction temperature to 70° C. The reaction was continued for further one hour, to thereby yield a crude chlorohydrin ether mixture.

The crude chlorohydrin ether mixture was added with stirring to 3.3 liters of a 16% aqueous sodium hydroxide solution heated at 90° C. over two hours. The mixture was stirred at 90° C. for further one hour, the heating was stopped, and the reaction batch was neutralized with 200 ml of 6 N hydrochloric acid. The neutralized reaction mixture was concentrated in a vacuum, precipitated salts were separated by filtration, the filtrate was diluted with water and subjected to desalting through a mixture of a cation-exchange resin and an anion-exchange resin. The temperature was then elevated to about 200° C., the system was gradually evacuated using a vacuum pump to increase the degree of vacuum, and the residual glycerol was removed to a content of 1 percent by weight or less. Thus, about 1000 g of a reaction product was obtained.

The prepared polyglycerol composition contains chlorine and is inferior in safety as a food additive.

Comparative Example 2

The reaction procedure of Example 1 was repeated, except for using no activated carbon catalyst. However, the reaction did not proceed, and no product was obtained.

TABLE 1

| | | | Ex. 1 | Ex. 2 | Com. Ex. 1 |
|---|---|---|---|---|---|
| Material | | Glycerol | mol | 10 | — | — |
| | | Diglycerol | mol | — | 10 | — |
| | | Glycidol | mol | 10 | 10 | — |
| | | Glycerol-α-monochlorohydrin | mol | — | — | 12 |
| | | Epichlorohydrin | mol | — | — | 12 |
| Catalyst | Type | | | Activated carbon | Activated carbon | SnCl$_4$ |
| | Amount to 100 parts by weight of glycidol | | part by weight | 1.1 | 1.3 | — |
| Polyglycerol | Composition | Glycerol | wt. % | 0 | 0.8 | 0.5 |
| | | Diglycerol | wt. % | 47.5 | 33.6 | 55 |
| | | Triglycerol | wt. % | 29.1 | 31.1 | 25 |
| | | Tetraglycerol | wt. % | 13.1 | 17 | 10 |
| | | Pentaglycerol | wt. % | 5.8 | 8.6 | 0.5 |
| | | Hexaglycerol | wt. % | 2.2 | 3.5 | 0.1 |
| | | Polyglycerols having a polymerization degree of 7 or higher | wt. % | 0.7 | 1.4 | 0.5 |
| | | Cyclic diglycerol | wt. % | 0.38 | 0.5 | 0.4 |
| | | Cyclic triglycerol | wt. % | 0.14 | 0.9 | 0.2 |
| | | Cyclic tetraglycerol | wt. % | 1.11 | 1.7 | 0.3 |
| | | Content of di-, tri-, and tetra-glycerols | wt. % | 89.66 | 81.7 | 90 |
| | | Content of cyclic polyglycerols | wt. % | 1.63 | 3.1 | 0.9 |
| | | Total | wt. % | 100 | 95.6 | 92.4 |
| | Properties | Chlorine content | ppm | <0.1 | <0.1 | 24 |
| | | Metal content | ppm | <0.1 | <0.1 | <0.1 |
| | | Acid value | KOH mg/g | 0.2 | 0.06 | 0.1 |
| | | Hydroxyl value | KOH mg/g | 1146 | 1132 | 1157 |
| | | Viscosity | mPa · s/40° C. | 8600 | 7600 | 7200 |
| | | Color | APHA | 20 | 10 | 20 |
| | | Water content | % | 0.22 | 0.39 | 0.25 |

What is claimed is:

1. A polyglycerol composition:
comprising diglycerol, triglycerol, and tetraglycerol each in a content of 5 percent by weight or more;
having a total content of diglycerol, triglycerol, and tetraglycerol of 75 percent by weight or more;
having a total content of higher polyglycerol components of 10 percent by weight or less, the higher polyglycerol components each having a degree of polymerization of 7 or higher; and
being substantially free from chlorine atom.

2. The polyglycerol composition according to claim 1, having a total content of cyclic polyglycerols of 10 percent by weight or less.

3. The polyglycerol composition of one of claims 1 and 2, wherein the contents of tin atom, titanium atom, zinc atom, aluminum atom, copper atom, magnesium atom, phosphorus atom, and sulfur atom are each less than 1 ppm.

4. A process of preparing a polyglycerol composition, comprising the step of reacting glycerol and/or a polyglycerol with glycidol in-the presence of an activated carbon catalyst.

5. The process of claim 4, further comprising reacting glycerol with glycidol in the presence of the activated carbon catalyst; and removing unreacted glycerol from the resulting polyglycerol composition.

6. The process of claim 4, further comprising reacting diglycerol with glycidol in the presence of the activated carbon catalyst.

7. The polyglycerol composition of claim 1, prepared by the process according to any one of claims 4 to 6.

* * * * *